United States Patent
Feng et al.

(10) Patent No.: US 10,767,474 B2
(45) Date of Patent: Sep. 8, 2020

(54) SURFACTANT SELECTION METHODS FOR WETTING ALTERATION IN SUBTERRANEAN FORMATIONS

(71) Applicant: Multi-Chem Group, LLC, San Angelo, TX (US)

(72) Inventors: Lijie Feng, Spring, TX (US); Liang Xu, The Woodlands, TX (US)

(73) Assignee: Multi-Chem Group, LLC, San Angelo, TX (US)

( * ) Notice: Subject to any disclaimer, the term of this patent is extended or adjusted under 35 U.S.C. 154(b) by 0 days.

(21) Appl. No.: 15/512,724

(22) PCT Filed: Nov. 13, 2014

(86) PCT No.: PCT/US2014/065533
§ 371 (c)(1),
(2) Date: Mar. 20, 2017

(87) PCT Pub. No.: WO2016/076877
PCT Pub. Date: May 19, 2016

(65) Prior Publication Data
US 2017/0292375 A1     Oct. 12, 2017

(51) Int. Cl.
*E21B 49/08*     (2006.01)
*E21B 43/26*     (2006.01)
(Continued)

(52) U.S. Cl.
CPC .............. *E21B 49/08* (2013.01); *C09K 8/584* (2013.01); *C09K 8/602* (2013.01); *E21B 21/062* (2013.01);
(Continued)

(58) Field of Classification Search
None
See application file for complete search history.

(56) References Cited

U.S. PATENT DOCUMENTS 4,799,547 A * 1/1989 Borchardt .............. C09K 8/594
166/270.1
9,518,449 B1 * 12/2016 Brady ................. E21B 41/0092
(Continued)

FOREIGN PATENT DOCUMENTS

WO     2008/117222 A1     10/2008

OTHER PUBLICATIONS

Liang, Chen. "Cationic and Anionic Carbon Dioxide Responsive Switchable Surfactants," Queen's University, Apr. 2010 (Year: 2010).*
(Continued)

*Primary Examiner* — Angela M DiTrani Leff
(74) *Attorney, Agent, or Firm* — Tenley Krueger; Baker Botts L.L.P.

(57) ABSTRACT

Systems and methods for selecting surfactants for use in subterranean formations are provided. In one embodiment, the methods comprise: providing a sample of oil from at least a portion of a subterranean formation; measuring at least one of the total acid number (TAN) and the total base number (TBN) of the oil sample; and selecting a set of surfactants to evaluate for a treatment in at least a portion of the subterranean formation based on at least one of the TAN and the TBN of the oil sample, the set of surfactants selected from the group consisting of: a set of cationic surfactants, a set of anionic surfactants, and a set of zwitterionic surfactants.

8 Claims, 5 Drawing Sheets

(51) Int. Cl.
| | |
|---|---|
| *E21B 21/06* | (2006.01) |
| *C09K 8/584* | (2006.01) |
| *C09K 8/60* | (2006.01) |
| *E21B 43/16* | (2006.01) |
| *E21B 43/25* | (2006.01) |
| *G01N 33/28* | (2006.01) |
| *E21B 43/20* | (2006.01) |
| *E21B 43/24* | (2006.01) |
| *E21B 43/267* | (2006.01) |

(52) U.S. Cl.
CPC .............. *E21B 43/16* (2013.01); *E21B 43/25* (2013.01); *E21B 43/26* (2013.01); *E21B 49/081* (2013.01); *G01N 33/2823* (2013.01); *E21B 43/168* (2013.01); *E21B 43/20* (2013.01); *E21B 43/24* (2013.01); *E21B 43/267* (2013.01)

(56) References Cited

U.S. PATENT DOCUMENTS

| | | | |
|---|---|---|---|
| 2004/0176478 A1 | 9/2004 | Dahayanake et al. | |
| 2010/0096129 A1 | 4/2010 | Hinkel et al. | |
| 2012/0097389 A1* | 4/2012 | Dwarakanath | C09K 8/58 166/270.1 |
| 2013/0067999 A1 | 3/2013 | Xu et al. | |
| 2013/0068457 A1* | 3/2013 | Thach | C07C 303/24 166/270.1 |
| 2013/0125630 A1* | 5/2013 | Collins | E21B 43/20 73/64.56 |
| 2013/0190543 A1* | 7/2013 | Barnes | C09K 8/584 585/4 |
| 2013/0296200 A1 | 11/2013 | Hernandez Altamirano et al. | |
| 2014/0124205 A1 | 5/2014 | Nasr-el-Din et al. | |
| 2014/0208826 A1* | 7/2014 | Larter | E21B 49/06 73/23.41 |
| 2015/0167437 A1* | 6/2015 | Dawson | E21B 27/00 166/250.1 |
| 2015/0354332 A1* | 12/2015 | Kurkal-Siebert | C09K 8/584 166/266 |
| 2016/0024372 A1* | 1/2016 | Fathi Najafabadi | C09K 8/58 166/250.02 |
| 2016/0272873 A1* | 9/2016 | Mahadevan | C09K 8/58 |
| 2016/0280986 A1* | 9/2016 | Xu | C09K 8/602 |

OTHER PUBLICATIONS

Standnes et al., Wettability alteration in chalk 2. Mechanism for wettability alteration from oil wet to water wet using surfactants, 2000, Journal of Petroleum Science and Engineering, 28, 123-143 (Year: 2000).*

Hou et al., Mechanistic study of wettability alteration of oil-wet sandstone surface using different surfactants, 2015, Applied Surface Science, 330, 56-64 (Year: 2015).*

Carbonate, Schlumberger Oilfield Glossary, retrieved Mar. 26, 2019 from https://www.glossary.oilfield.slb.com/Terms/c/carbonate.aspx (Year: 2019).*

Core testing, Schlumberger Oilfield Glossary, retrieved Mar. 26, 2019 from https://www.glossary.oilfield.slb.com/Terms/c/carbonate. aspx (Year: 2019).*

Nazarova, Marfa, Wettability Study Through X-Ray Micro-CT Pore Space Imagine in EOR Applied to LSB Recovery Process, Oct. 30, 2014 (Year: 2014).*

Hendraningrat, Luky,et al. Effects of the initial Rock WEttability on Silica-Based Nanofluid-Enhanced Oil Recovery Processes at Reservoir Temperatures,Aug. 26, 2014, ACS Publications, 2014 American Chemical Society, p. 6228-6241 (Year: 2014).*

Cissokho, et al., Low Salinity Oil Recovery on Clayey Sandstone: Experimental Study, Sep. 2009, University of Bordeaux, p. 1-12 (Year: 2009).*

Salehi, Mehdi, Stephen J. Johnson, and Jenn-Tai Liang. "Mechanistic study of wettability alteration using surfactants with applications in naturally fractured reservoirs." Langmuir 24.24 (2008): 14099-14107.

Hammond, Paul S., and Evren Unsal. "Spontaneous Imbibition of Surfactant Solution into an Oil-Wet Capillary: Wettability Restoration by Surfactant-Contaminant Complexation." Langmuir 27.8 (2011): 4412-4429.

Hammond, Paul S., and Evren Unsal. "Spontaneous and forced imbibition of aqueous wettability altering surfactant solution into an initially oil-wet capillary." Langmuir 25.21 (2009): 12591-12603.

Stoll, Martin, et al. "Toward field-scale wettability modification— the limitations of diffusive transport" SPE Reservoir Evaluation & Engineering 11.03 (2008): 633-640.

Xu, Liang, and Qiang Fu. "Ensuring better well stimulation in unconventional oil and gas formations by optimizing surfactant additives." SPE Paper 154212, SPE Western Regional Meeting. Society of Petroleum Engineers, 2012.

Standnes, Dag C., and Tor Austad. "Wettability alteration in chalk: 2. Mechanism for wettability alteration from oil-wet to water-wet using surfactants." Journal of Petroleum Science and Engineering 28.3 (2000): 123-143.

Buckley, J. S., Y. Liu, and S. Monsterleet. "Mechanisms of wetting alteration by crude oils." SPE Journal 3.01 (1998): 54-61.

Rigzone.com, "What is EOR, and How Does It Work?", http://www.rigzone.com/training/insight_pf.asp?i_id=313.

Nalco/Tiorco Brochure "ASP/SP—Alkaline Surfactant Polymer/Surfactant Polymer Technologies", 4 pages.

International Search Report and Written Opinion issued in related PCT Application No. PCT/US2014/065533 dated Jul. 22, 2015, 16 pages.

International Preliminary Report on Patentability issued in related Application No. PCT/US2014/065533, dated May 26, 2017 (12 pages).

Feng, Lijie & Xu, Liang. (2015). Implications of Shale Oil Compositions on Surfactant Efficacy for Wettability Alteration. 10.2118/172974-MS.

* cited by examiner

SURFACTANT SELECTION METHODS FOR WETTING ALTERATION IN SUBTERRANEAN FORMATIONS

CROSS-REFERENCE TO RELATED APPLICATION

The present application is a U.S. National Stage Application of International Application No. PCT/US2014/065533 filed Nov. 13, 2014, which is incorporated herein by reference in its entirety for all purposes.

BACKGROUND

The present disclosure relates to systems and methods for treating subterranean formations.

Natural resources such as gas, oil, and water residing in a subterranean formation or zone are usually recovered by drilling a wellbore down to the subterranean formation while circulating a drilling fluid in the wellbore. After terminating the circulation of the drilling fluid, a string of pipe, e.g., casing, is run in the wellbore and cemented into place. Thereafter, one or more treatments may be performed in the subterranean formation and/or the well bore to facilitate the production of hydrocarbons such as gas and oil from the well, such as enhanced oil recovery operations, stimulation treatments (e.g., hydraulic fracturing), and the like. For example, an enhanced oil recovery operation is a generic term for techniques for increasing the amount of crude oil that can be extracted from a hydrocarbon-producing formation (e.g., hydrocarbon reservoirs). Such operations can be particularly useful in unconventional reservoirs (e.g., shale) where the extraction of such hydrocarbons may not be facilitated by natural buoyant forces.

In order to accomplish these treatments more effectively, one or more surfactants or emulsifiers may be injected into the formation, among other reasons, to lower the interfacial tension between oil and water which allows stable emulsions with small drops to be formed that can be carried out of the formation with the fluid. Conventional selection for selecting a surfactant typically focuses on one or two attributes of the surfactant. In particular for unconventional oil and gas plays, efficacy of the surfactant chosen for hydraulic fracturing may depend on a number of factors, including formation characteristics, oil types, reservoir temperature, and the other elements of the fracturing fluid. In some instances, a screening process comprising a set of experimental tests evaluating dynamic surface tension, interfacial surface tension, oil recovery tests, and/or wettability/imbibition tests has be used to evaluate surfactant performance for use in unconventional reservoirs prior to their use to identify surfactants that are more likely to maximize production and reduce risk of formation damage. However, these screening processes can be lengthy and tedious when used to screen large numbers of potential surfactants for use in a particular formation.

BRIEF DESCRIPTION OF THE DRAWINGS

These drawings illustrate certain aspects of some of the embodiments of the present disclosure, and should not be used to limit or define the claims.

Figure 1:
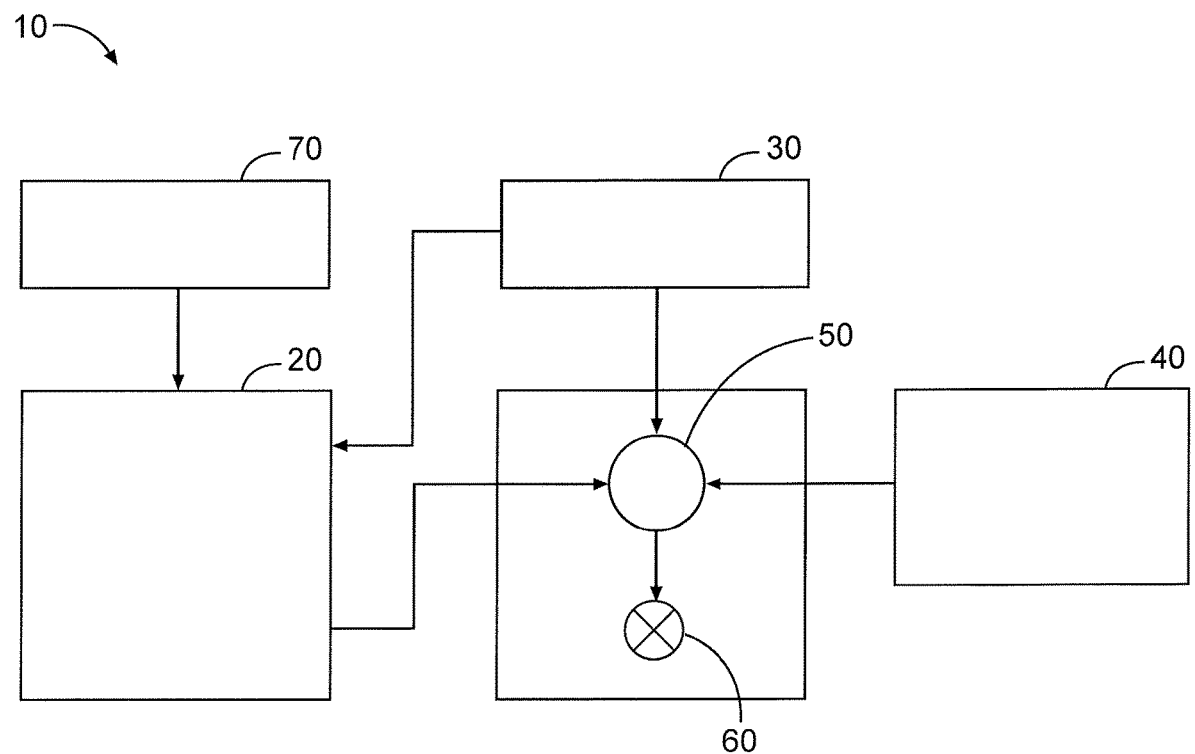
FIG. 1 is a diagram illustrating an example of a fracturing system that may be used in accordance with certain embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

The present disclosure relates to systems and methods for treating subterranean formations. More particularly, the present disclosure relates to systems and methods for selecting surfactants for use in subterranean formations, e.g., in well stimulation and/or enhanced oil recovery operations.

The present disclosure provides methods and systems for selecting surfactants for use in a particular subterranean formation based at least in part on the total acid number (TAN) and/or the total base number (TBN) of an oil sample obtained from a portion of that formation. As used herein, the "total acid number" of a sample refers to the milligrams of a standard base (typically potassium hydroxide) needed to neutralize the amount of acid per gram of the sample. As used herein, the "total base number" of a sample refers to the milligrams of a standard base (typically potassium hydroxide) equivalent to the moles of basic components in the sample per gram of the sample. The TAN and TBN values for an oil sample are each measures of the amounts of acidic or basic components in a sample. In particular, the TAN and/or TBN of the oil sample (including the ratio of those two values) may be used to limit the surfactants screened for use in the formation to cationic, anionic, or zwitterionic surfactants having a polarity opposite that of the oil in the sample. In certain embodiments, if an oil sample exhibits a high TAN (e.g., greater than its TBN), cationic surfactants may be evaluated for use in the source formation without evaluating any anionic surfactants. Conversely, if an oil sample exhibits a TBN (e.g., greater than its TAN), anionic surfactants may be evaluated for use in the source formation without evaluating any cationic surfactants. In certain embodiments, if an oil sample exhibits a high TAN and a high TBN, zwitterionic surfactants may be evaluated for use in the source formation without evaluating any cationic or anionic surfactants. In certain embodiments, carbonate formations may produce oils having higher TAN values, while sandstone formations may produce oils having higher TBN values. The methods and compositions of the present disclosure also may be used in formations comprising shales and/or clays.

In the methods of the present disclosure, the TAN and/or TBN may be considered alone or along with other conditions, parameters, and/or sample tests from a portion of the subterranean formation in selecting one or more treating surfactants for use in the formation. The treating surfactant(s) selected according to the methods of the present disclosure may be introduced into at least a portion of a subterranean formation (for example, as a component of a treatment fluid that is pumped or injected into a subterranean formation) in the course of one or more treatments therein. In certain embodiments, the treating surfactant(s) of the present disclosure may be included in a treatment fluid (e.g., a pad fluid and/or fracturing fluid) that is introduced into a formation in the course of one or more stimulation treatments (such as fracturing treatments, acidizing treatments, etc.) or an enhanced oil recovery operation.

It has been previously suggested that two primary mechanisms were responsible for how surfactants alter rock wettability to improve oil production: ion pair coupling between surfactant and polar compounds in the oil ("cleaning"), and surfactant adsorption onto the rock surface ("coating"). Without limiting the disclosure to any particular theory or mechanism, it is believed that the cationic or anionic surfactants selected according to the methods of the present disclosure will electrostatically interact with polar compounds of an opposite polarity in crude oil to form ion pairs and, in turn, the ion pairs will remove any oil components adsorbed onto a rock surface to make the rock surface water wet.

Among the many potential advantages to the methods and compositions of the present disclosure, only some of which are alluded to herein, the methods, compositions, and systems of the present disclosure may facilitate the evaluation and/or selection of surfactants for use in treating subterranean formations. These methods may be particularly advantageous in unconventional reservoirs such as shale and/or tight gas formations, where stimulation and enhanced oil recovery operations are used to facilitate the production of oil and gas. In certain embodiments, the methods and systems of the present disclosure may enable the selection of surfactants that will alter the wettability of rock surfaces more quickly than other selection methods. For example, by focusing on surfactants that leverage the "cleaning" mechanism described above, it may not be necessary for the surfactant to accumulate in a sufficient amount to form a coating on the rock surface before it can alter the wettability of certain portions of the rock.

The cationic, anionic, and/or zwitterionic (also sometimes referred to as amphoteric) surfactants selected and/or used in the methods and systems of the present disclosure may comprise any such surfactants known in the art. Examples of cationic surfactants that may be suitable for use in certain embodiments of the present disclosure include, but are not limited to, alkyl amines, alkyl amine salts, quaternary ammonium salts such as trimethyltallowammonium halides (e.g., trimethyltallowammonium chloride, trimethyltallowammonium bromide), amine oxides, alkyltrimethyl amines, triethyl amines, alkyldimethylbenzylamines, cetyltrimethylammonium bromide, alkyl dimethyl benzyl-ammonium chloride, trimethylcocoammonium chloride, derivatives thereof, and combinations thereof. Examples of anionic surfactants that may be suitable for use in certain embodiments of the present disclosure include, but are not limited to, alkyl carboxylates, alkylether carboxylates, N-acylaminoacids, N-acylglutamates, N-acylpolypeptides, alkylbenzenesulfonates, paraffinic sulfonates, α-olefinsulfonates, lignosulfates, derivatives of sulfosuccinates, polynapthylmethylsulfonates, alkyl sulfates, alkylethersulfates, C8 to C22 alkylethoxylate sulfate, alkylphenol ethoxylate sulfate (or salts thereof), monoalkylphosphates, polyalkylphosphates, fatty acids, alkali salts of fatty acids, glyceride sulfates, sodium salts of fatty acids, soaps, derivatives thereof, and combinations thereof. Examples of amphoteric or zwitterionic surfactants that may be suitable for use in certain embodiments of the present disclosure include, but are not limited to, dihydroxyl alkyl glycinate, alkyl ampho acetate or propionate, alkyl betaine, alkyl amidopropyl betaine and alkylimino mono- or di-propionates derived from certain waxes, fats and oils.

In certain embodiments, the cationic, anionic, and/or zwitterionic surfactant(s) selected according to the methods of the present disclosure may be used in combination with one or more additional surfactants, including but not limited to amphoteric surfactants, zwitterionic surfactants, nonionic surfactants, and combinations thereof. Examples of nonionic surfactants that may be suitable for use in certain embodiments of the present disclosure include, but are not limited to, alcohol oxylalkylates, alkyl phenol oxylalkylates, nonionic esters such as sorbitan esters alkoxylates of sorbitan esters, castor oil alkoxylates, fatty acid alkoxylates, lauryl alcohol alkoxylates, nonylphenol alkoxylates, octylphenol alkoxylates, and tridecyl alcohol alkoxylate, derivatives thereof, and combinations thereof. The inclusion and/or selection of such nonionic surfactants may depend on, among other things, additional experiments or tests performed to evaluate one or more properties of the surfactant and/or its interaction with rock surfaces and/or oil in the subterranean formation. A person of skill in the art with the benefit of the present disclosure will understand when such surfactants may be suitable and how to select such surfactants that may be suitable for a particular application of the methods of the present disclosure.

As mentioned above, the methods and systems of the present disclosure may involve the use of one or more additional experimental tests to evaluate the cationic, anionic, and/or zwitterionic surfactants as selected according to the TAN/TBN values of an oil sample from the formation. In certain embodiments, those tests may include, but are not limited to water solubility tests, emulsion tendency tests, interfacial surface tension measurements, wettability-spontaneous imbibition tests, oil recovery tests, proppant adsorption tests, and the like. A person of ordinary skill in the art, with the benefit of this disclosure, will recognize when such additional tests are useful and the appropriate tests or combination thereof to use in evaluating surfactants for a particular application of the present disclosure.

As noted above, the treating surfactant(s) selected according to the methods of the present disclosure may be incorporated into a treatment fluid that is introduced into at least a portion of a subterranean formation, for example, through a well bore. The treatment fluids used may comprise any base fluid known in the art, including aqueous base fluids, non-aqueous base fluids, and any combinations thereof. Aqueous fluids that may be suitable for use in the methods and systems of the present disclosure may comprise water from any source. Such aqueous fluids may comprise fresh water, salt water (e.g., water containing one or more salts dissolved therein), brine (e.g., saturated salt water), seawater, or any combination thereof. In most embodiments of the present disclosure, the aqueous fluids comprise one or more ionic species, such as those formed by salts dissolved in water. For example, seawater and/or produced water may comprise a variety of divalent cationic species dissolved therein. In certain embodiments, the density of the aqueous fluid can be adjusted, among other purposes, to provide additional particulate transport and suspension in the compositions of the present disclosure. In certain embodiments, the pH of the aqueous fluid may be adjusted (e.g., by a buffer or other pH adjusting agent) to a specific level, which may depend on, among other factors, the types of viscosifying agents, acids, and other additives included in the fluid. One of ordinary skill in the art, with the benefit of this disclosure, will recognize when such density and/or pH adjustments are appropriate. Examples of non-aqueous fluids that may be suitable for use in the methods and systems of the present disclosure include, but are not limited to, oils, hydrocarbons, organic liquids, and the like. In certain embodiments, the fracturing fluids may comprise a mixture of one or more fluids and/or gases, including but not limited to emulsions, foams, and the like.

In certain embodiments, the treatment fluids used in the methods and systems of the present disclosure optionally may comprise any number of additional additives. Examples of such additional additives include, but are not limited to, salts, acids, proppant particulates, diverting agents, fluid loss control additives, gas, nitrogen, carbon dioxide, surface modifying agents, tackifying agents, foamers, corrosion inhibitors, scale inhibitors, catalysts, clay control agents, biocides, friction reducers, antifoam agents, bridging agents, flocculants, additional $H_2S$ scavengers, $CO_2$ scavengers, oxygen scavengers, lubricants, additional viscosifiers, breakers, weighting agents, relative permeability modifiers, resins, wetting agents, coating enhancement agents, filter cake removal agents, antifreeze agents (e.g., ethylene glycol), and the like. A person skilled in the art, with the benefit of this disclosure, will recognize the types of additives that may be included in the fluids of the present disclosure for a particular application.

In the methods and systems of the present disclosure, a sample of oil from a portion of a subterranean formation to be treated may be obtained and its TAN and/or TBN may be measured using any suitable method or equipment known in the art. For example, in certain embodiments, an oil sample may be extracted from a portion of the subterranean formation and sent to an offsite laboratory for evaluation, including measurement of its TAN and/or TBN. In other embodiments, the TAN and/or TBN of an oil sample may be evaluated at a well site from which it was obtained, for example, in a mobile laboratory or using a portable test kit. Information obtained from these evaluations may be used to select and/or exclude surfactants by personnel at an offsite location, at the site where the sample was obtained, and/or at the site where a treatment using the surfactant is to be performed.

The present disclosure provides methods for using the treatment fluids comprising one or more surfactants selected using the methods of the present disclosure to carry out a variety of subterranean treatments, including but not limited to, well stimulation treatments (e.g., hydraulic fracturing treatments, matrix acidizing treatments, fracture acidizing or "acid frac" treatments, etc.), drilling operations, and enhanced oil recovery operations. In some embodiments, the treatment fluid may be introduced at a pressure sufficient to create or enhance one or more fractures within the subterranean formation (e.g., hydraulic fracturing). In some embodiments, the treatment fluids comprising one or more surfactants selected according to the methods of the present disclosure may be used in treating a portion of a subterranean formation, for example, in acidizing treatments such as matrix acidizing or fracture acidizing.

In some embodiments, a treatment fluid comprising one or more surfactants selected using the methods of the present disclosure may be introduced into a subterranean formation as a part of an enhanced oil recovery operation, which may include water flooding treatments, gas injection treatments, foam injection treatments, chemical injection treatments, microbial injection treatments, or thermal recovery treatments (which includes cyclic or continuous steam, steam flooding, and fire flooding). In certain of these enhanced oil recovery operations, a treatment fluid comprising water, carbon dioxide, or other fluids that further comprises one or more surfactants selected according to embodiments of the present disclosure may be injected into a well bore (e.g., an injection well) that penetrates the subterranean formation. That treatment fluid or another fluid introduced behind it may be injected into the formation using one or more pumps at a pressure sufficient to pressurize the formation and drive hydrocarbons such as crude oil or gas toward a second well (e.g., a production well) that penetrates another portion of the subterranean formation. The hydrocarbons and the treatment fluid or solution may then be produced out of the second well. The surfactants in the treatment fluid may, among other things, lower interfacial tension and/or alter the wettability of the rock surfaces in the formation to facilitate the movement of oil toward a producing well.

Certain embodiments of the methods and compositions disclosed herein may directly or indirectly affect one or more components or pieces of equipment associated with the preparation, delivery, recapture, recycling, reuse, and/or disposal of the disclosed compositions. For example, and with reference to FIG. 1, the disclosed methods and compositions may directly or indirectly affect one or more components or pieces of equipment associated with an exemplary fracturing system 10, according to one or more embodiments. In certain instances, the system 10 includes a fracturing fluid producing apparatus 20, a fluid source 30, a proppant source 40, and a pump and blender system 50 and resides at the surface at a well site where a well 60 is located. In certain instances, the fracturing fluid producing apparatus 20 combines a gel pre-cursor with fluid (e.g., liquid or substantially liquid) from fluid source 30, to produce a hydrated fracturing fluid that is used to fracture the formation. The hydrated fracturing fluid can be a fluid for ready use in a fracture stimulation treatment of the well 60 or a concentrate to which additional fluid is added prior to use in a fracture stimulation of the well 60. In other instances, the fracturing fluid producing apparatus 20 can be omitted and the fracturing fluid sourced directly from the fluid source 30. In certain instances, the fracturing fluid may comprise water, a hydrocarbon fluid, a polymer gel, foam, air, wet gases and/or other fluids.

The proppant source 40 can include a proppant for combination with the fracturing fluid. The system may also include additive source 70 that provides one or more additives (e.g., gelling agents, weighting agents, surfactants, and/or other optional additives) to alter the properties of the fracturing fluid. For example, the other additives 70 can be included to reduce pumping friction, to reduce or eliminate the fluid's reaction to the geological formation in which the well is formed, to operate as surfactants, and/or to serve other functions.

The pump and blender system 50 receives the fracturing fluid and combines it with other components, including proppant from the proppant source 40 and/or additional fluid from the additives 70. The resulting mixture may be pumped down the well 60 under a pressure sufficient to create or enhance one or more fractures in a subterranean zone, for example, to stimulate production of fluids from the zone. Notably, in certain instances, the fracturing fluid producing apparatus 20, fluid source 30, and/or proppant source 40 may be equipped with one or more metering devices (not shown) to control the flow of fluids, proppants, and/or other compositions to the pumping and blender system 50. Such metering devices may permit the pumping and blender system 50 can source from one, some or all of the different sources at a given time, and may facilitate the preparation of fracturing fluids in accordance with the present disclosure using continuous mixing or "on-the-fly" methods. Thus, for example, the pumping and blender system 50 can provide just fracturing fluid into the well at some times, just proppants at other times, and combinations of those components at yet other times.

Figure 2:
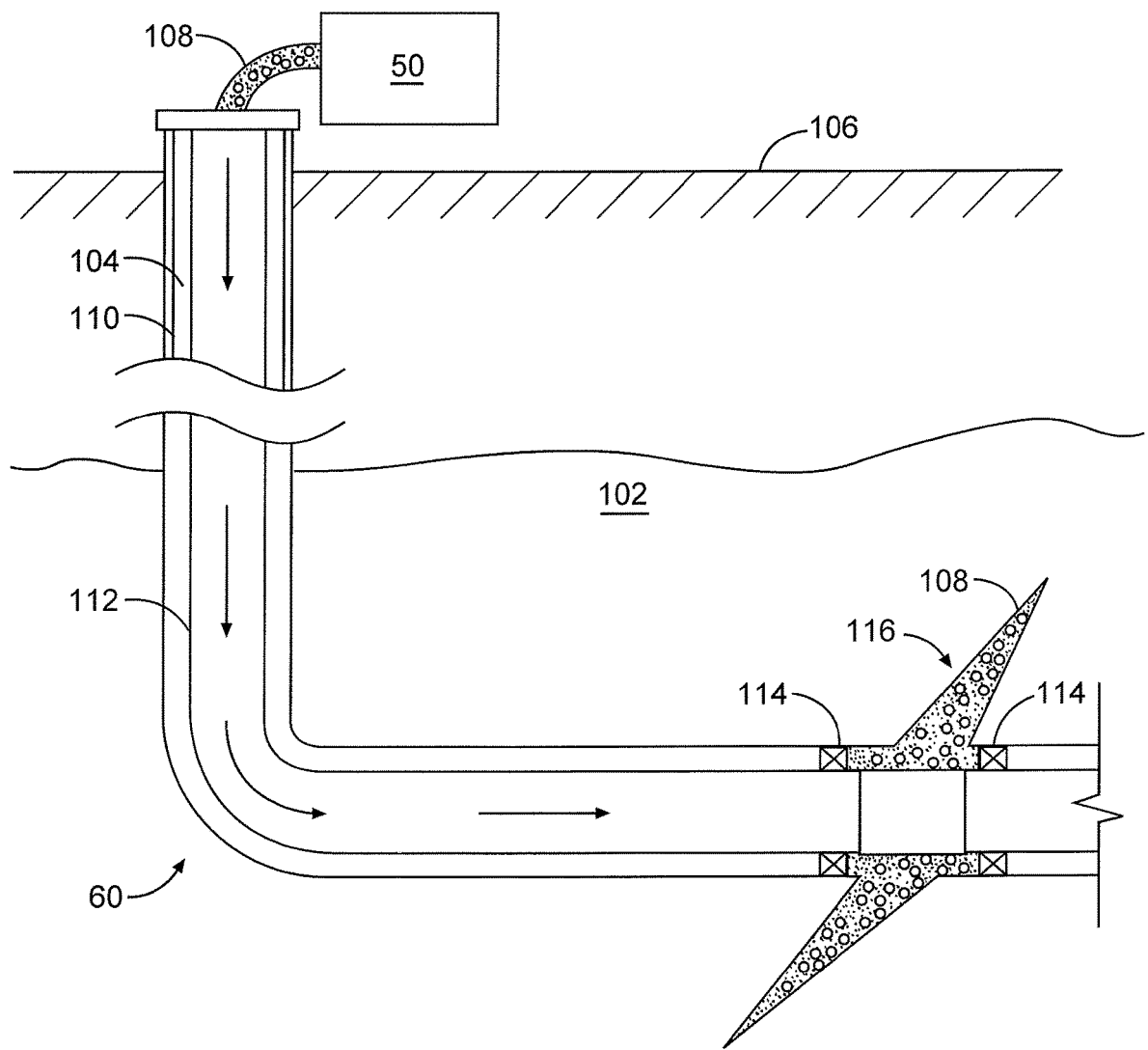
FIG. 2 is a diagram illustrating an example of a subterranean formation in which a fracturing operation may be performed in accordance with certain embodiments of the present disclosure.
Figure 3A:
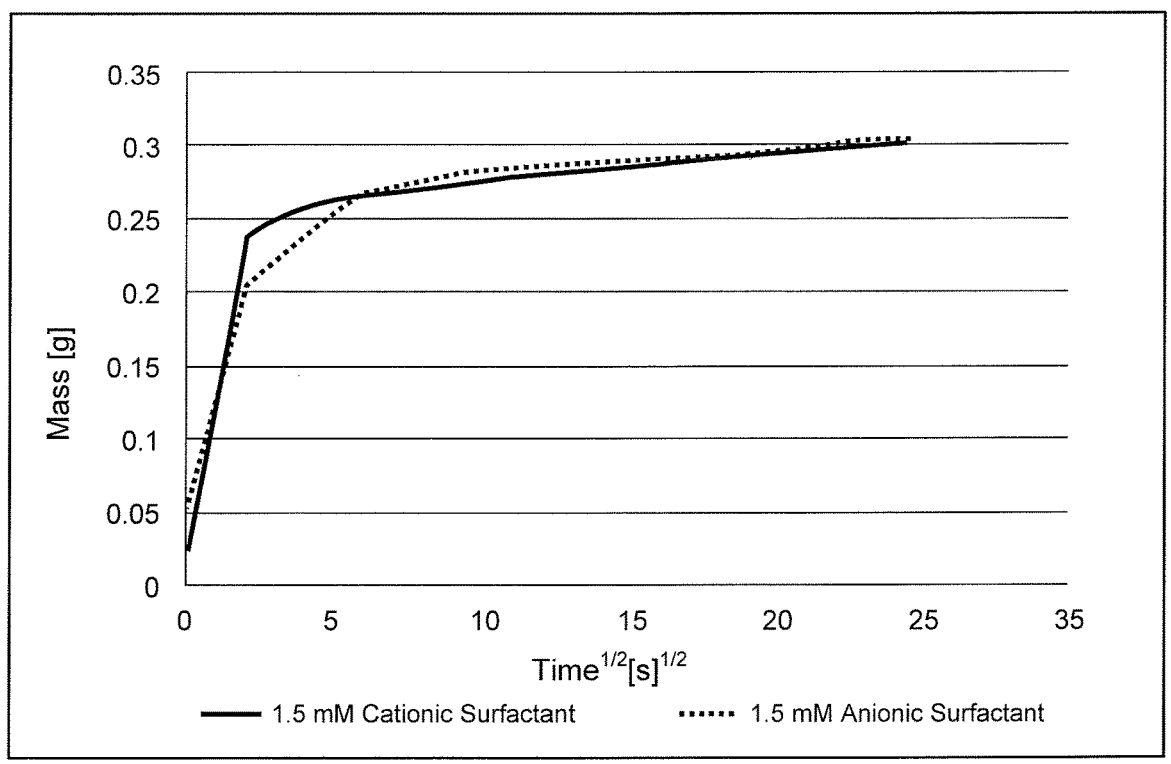
FIGS. 3A through 3D are graphs illustrating data from certain imbibition tests performed using surfactants according to certain embodiments of the present disclosure.
Figure 3B:
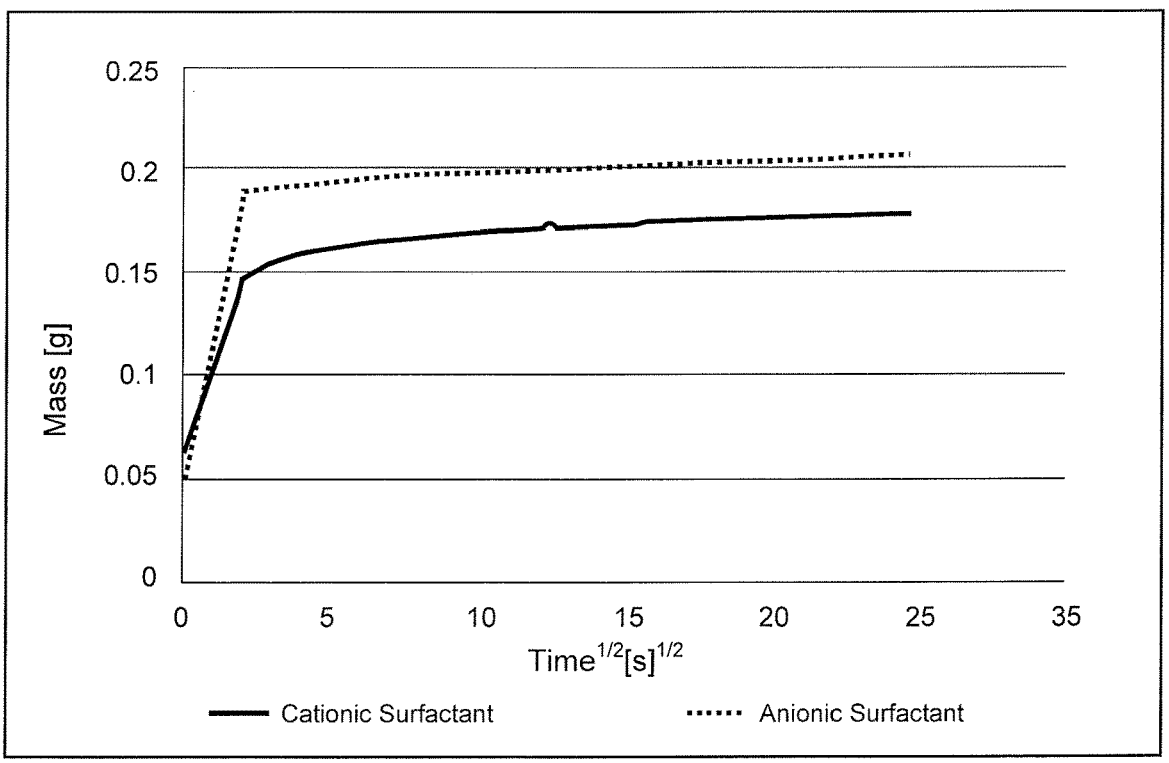
Figure 3C:
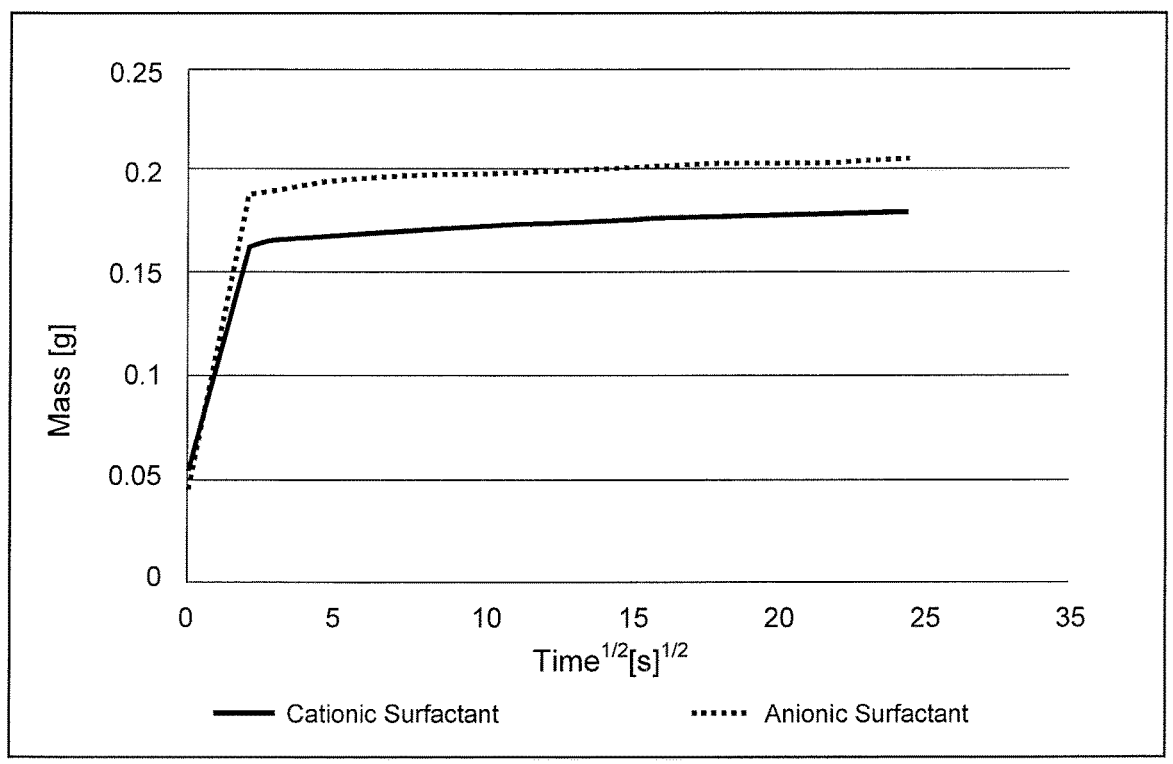
Figure 3D:
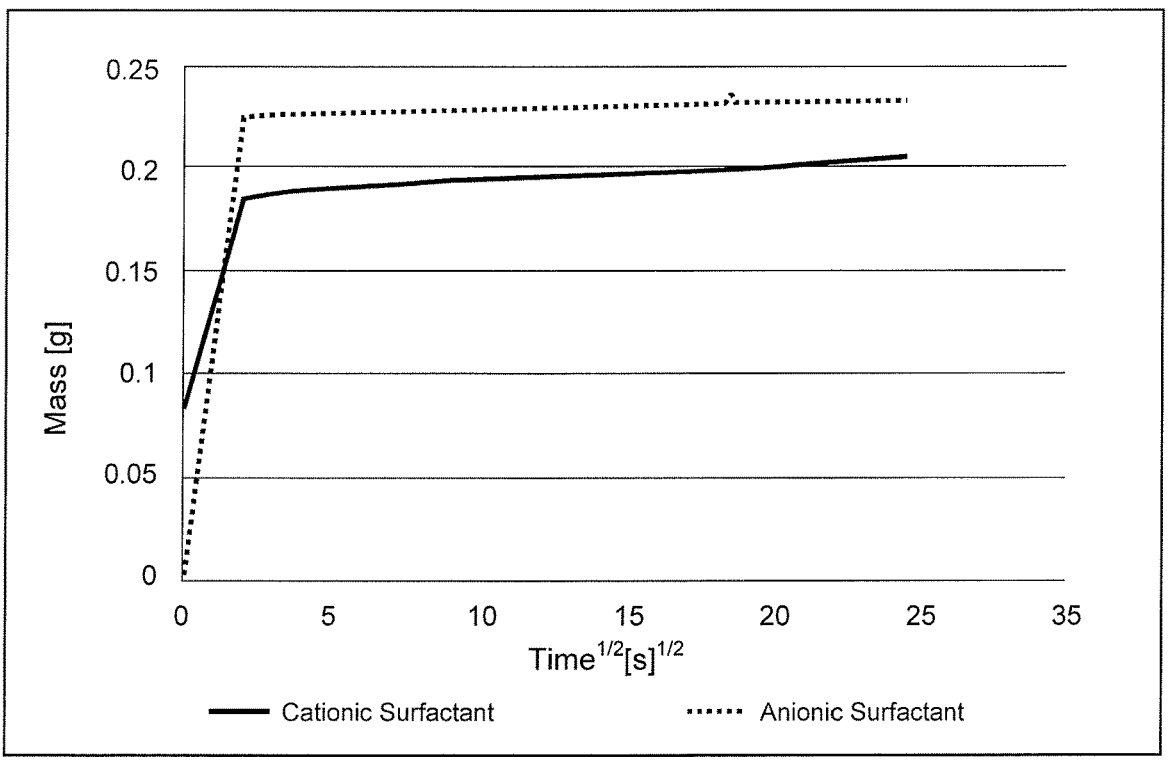

FIG. 2 shows the well 60 during a fracturing operation in a portion of a subterranean formation of interest 102 surrounding a well bore 104. The well bore 104 extends from the surface 106, and the fracturing fluid 108 is applied to a portion of the subterranean formation 102 surrounding the horizontal portion of the well bore. Although shown as vertical deviating to horizontal, the well bore 104 may include horizontal, vertical, slant, curved, and other types of well bore geometries and orientations, and the fracturing treatment may be applied to a subterranean zone surrounding any portion of the well bore. The well bore 104 can include a casing 110 that is cemented or otherwise secured to the well bore wall. The well bore 104 can be uncased or include uncased sections. Perforations can be formed in the casing 110 to allow fracturing fluids and/or other materials to flow into the subterranean formation 102. In cased wells, perforations can be formed using shape charges, a perforating gun, hydro jetting and/or other tools.

The well is shown with a work string 112 depending from the surface 106 into the well bore 104. The pump and blender system 50 is coupled a work string 112 to pump the fracturing fluid 108 into the well bore 104. The working string 112 may include coiled tubing, jointed pipe, and/or other structures that allow fluid to flow into the well bore 104. The working string 112 can include flow control devices, bypass valves, ports, and or other tools or well devices that control a flow of fluid from the interior of the working string 112 into the subterranean zone 102. For example, the working string 112 may include ports adjacent the well bore wall to communicate the fracturing fluid 108 directly into the subterranean formation 102, and/or the working string 112 may include ports that are spaced apart from the well bore wall to communicate the fracturing fluid 108 into an annulus in the well bore between the working string 112 and the well bore wall.

The working string 112 and/or the well bore 104 may include one or more sets of packers 114 that seal the annulus between the working string 112 and well bore 104 to define an interval of the well bore 104 into which the fracturing fluid 108 will be pumped. FIG. 2 shows two packers 114, one defining an uphole boundary of the interval and one defining the downhole end of the interval. When the fracturing fluid 108 is introduced into well bore 104 (e.g., in FIG. 2, the area of the well bore 104 between packers 114) at a sufficient hydraulic pressure, one or more fractures 116 may be created in the subterranean zone 102. The proppant particulates in the fracturing fluid 108 may enter the fractures 116 where they may remain after the fracturing fluid flows out of the well bore. These proppant particulates may "prop" fractures 116 such that fluids may flow more freely through the fractures 116.

While not specifically illustrated herein, the disclosed methods and compositions may also directly or indirectly affect any transport or delivery equipment used to convey the compositions to the fracturing system 10 such as, for example, any transport vessels, conduits, pipelines, trucks, tubulars, and/or pipes used to fluidically move the compositions from one location to another, any pumps, compressors, or motors used to drive the compositions into motion, any valves or related joints used to regulate the pressure or flow rate of the compositions, and any sensors (i.e., pressure and temperature), gauges, and/or combinations thereof, and the like.

To facilitate a better understanding of the present disclosure, the following examples of certain aspects of preferred embodiments are given. The following examples are not the only examples that could be given according to the present disclosure and are not intended to limit the scope of the disclosure or claims.

EXAMPLES

The TANs and TBNs of several different samples of oils from various shale plays throughout the United States were measured according to the modified ASTM D664 method and the ASTM D4739 method, and are listed in Table 1 below. Certain of these oil samples were used for the tests described in Examples 1-3 below.

TABLE 1

| Sample No. | Oil Source | TAN (mg KOH/ g Oil) | TBN (mg KOH/ g Oil) |
| --- | --- | --- | --- |
| 1 | Eagle Ford #1 | 3.07 | 0.05 |
| 2 | Williams Fork | 0.96 | 9.54 |
| 3 | Woodford | 0.01 | 0.16 |
| 4 | Wolfcamp #1 | 0.01 | 0.62 |
| 5 | Niobrara | 0.01 | 0.46 |
| 6 | Wolfcamp #2 | 0.01 | 0.89 |
| 7 | Eagle Ford #2 | 0.01 | 1.97 |

Example 1

Emulsion tendency tests were performed on several of the oil samples listed in Table 1. In some circumstances, surfactants that form weak emulsions may be more desirable in oil recovery treatments, since more stable emulsions may cause formation damage and/or reduce the effective area through which oil in a formation can flow. Portions of Samples 1, 2, 3, 4, and 7 were each placed in 2 different test vials; one of which contained a 1.5 mM aqueous solution of a cationic surfactant, and the other contained a 1.5 mM aqueous solution of an anionic surfactant. (The surfactant solutions had been prepared in DI water the night before, and then left in an oven at 80° C. overnight prior to the addition of the oil samples.) The test vials were capped and shaken to form an emulsion, and then allowed to stand after shaking to observe the stability of each emulsion formed. For Oil Samples 2, 3, 4, and 7, the emulsions in the anionic surfactant solutions broke more quickly than those in the cationic surfactant solutions. In contrast, for Oil Sample 1, the emulsion in the cationic solution broke more quickly. Thus, these tests demonstrated that surfactants having a polarity opposite of that of the oil were generally more effective at forming weak emulsions that broke more quickly than surfactant solutions of the same polarity as the oil.

Example 2

Next, imbibition tests were conducted using the Washburn method with a Kruss K100 tensiometer at room temperature to measure the ability of cationic and anionic surfactants (1.5 mM solutions of each) to alter the wettability of an oil-wet rock surface over time. The tests were performed using 1.5 g sandstone cores saturated with portions of Oil Samples 5, 6, and 7 and a 1.5 g limestone core saturated with a portion of Oil Sample 1. As shown in FIGS. 3A, 3B, 3C, and 3D, the mass of aqueous surfactant in the oil phase of each sample was plotted as a function of time ($s^{1/2}$). The slopes during the initial penetration of the cationic and anionic surfactants were calculated for each sample and are reported in Table 2 below.

TABLE 2

| Sample No. | FIG. | Slope for Cationic Surfactant | Slope for Anionic Surfactant |
|---|---|---|---|
| 1 | 3A | 0.1100 | 0.0769 |
| 5 | 3B | 0.0430 | 0.0724 |
| 6 | 3C | 0.0543 | 0.0718 |
| 7 | 3D | 0.0518 | 0.1122 |

The initial slope of the surfactant imbibition profile may reflect the penetration power of the surfactant, and thus its ability to alter the wettability of the surface. Thus, this test demonstrated that, for certain rock surfaces saturated with oil containing more acidic polar compounds, a cationic surfactant may alter the wettability of the surface more effectively, while an anionic surfactant may more effectively alter the wettability of a surface oil-wet with oil containing more basic polar compounds.

Example 3

Figure 4A:
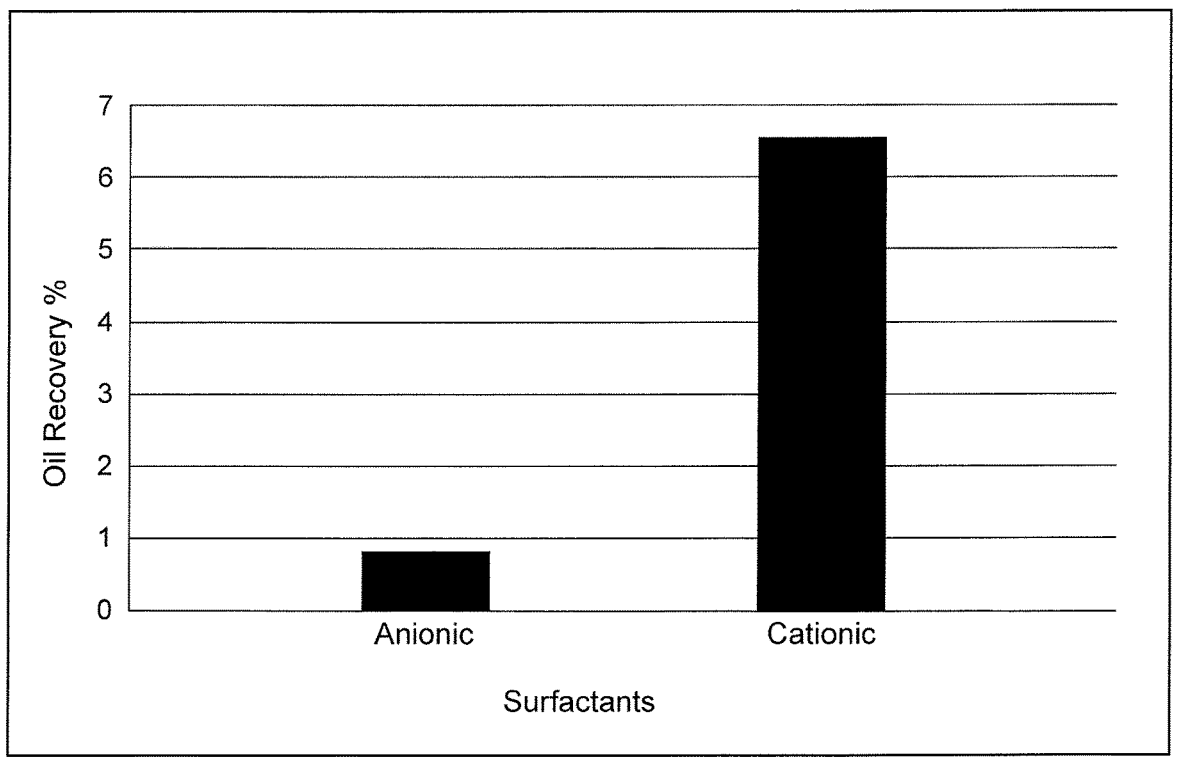
FIGS. 4A and 4B are graphs illustrating data from certain oil recovery tests using surfactants according to certain embodiments of the present disclosure.
Figure 4B:
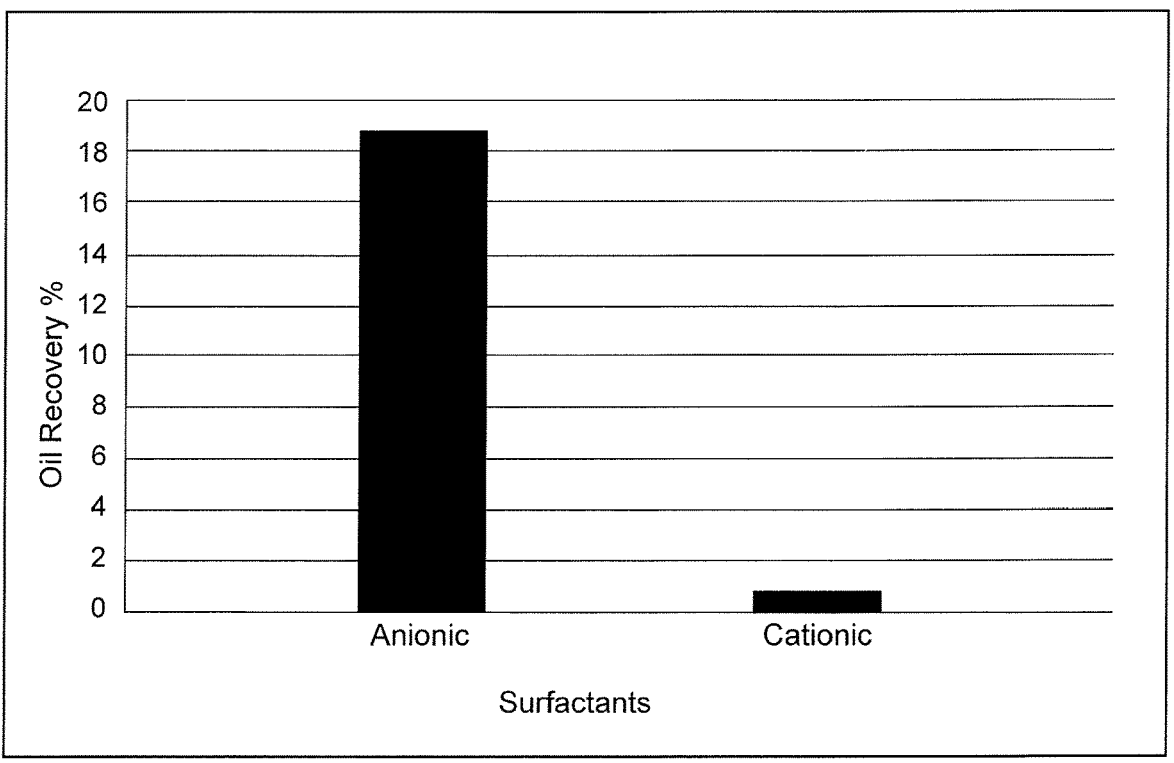

Finally, oil recovery tests were performed using Oil Samples 1 and 2. Sample 1 was tested using a crushed Indiana limestone core and Sample 2 was tested using a crushed Berea sandstone core. The cores were saturated with the oil samples at 80° C. for two weeks, dried in an oven at the same temperature, and were then packed into columns. Two 3-hour stages of a 1.5 mM aqueous solution of a cationic or anionic surfactant were injected into each core at 80° C. The percentage of oil extracted in each of the second stages (which is believed to correspond to the oil inside the pore spaces of the core) was measured, the results of which are reported in FIGS. 4A and 4B. Thus, this example demonstrates that higher oil recovery rates may be achieved using surfactants having a polarity opposite that of the polar compounds in an oil.

An embodiment of the present disclosure is a method comprising: providing a sample of oil from at least a portion of a subterranean formation; measuring at least one of the total acid number (TAN) and the total base number (TBN) of the oil sample; and selecting a set of surfactants to evaluate for a treatment in at least a portion of the subterranean formation based on at least one of the TAN and the TBN of the oil sample, the set of surfactants selected from the group consisting of: a set of cationic surfactants, a set of anionic surfactants, and a set of zwitterionic surfactants.

Another embodiment of the present disclosure is a method comprising: providing a sample of oil from at least a portion of a subterranean formation; measuring at least one of the total acid number (TAN) and the total base number (TBN) of the oil sample, wherein the TAN of the oil sample is greater than the TBN of the oil sample; and evaluating one or more cationic surfactants for a treatment in at least a portion of the subterranean formation.

Another embodiment of the present disclosure is a method comprising: providing a sample of oil from at least a portion of a subterranean formation; measuring at least one of the total acid number (TAN) and the total base number (TBN) of the oil sample, wherein the TBN of the oil sample is greater than the TAN of the oil sample; and evaluating one or more anionic surfactants for a treatment in at least a portion of the subterranean formation.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:

1. A method comprising:
providing a sample of oil from at least a portion of a subterranean formation;
determining the total acid number (TAN) and the total base number (TBN) of the oil sample by measuring the TAN and the TBN at a site where a well bore penetrating at least a portion of the subterranean formation is located, wherein the TAN of the oil sample is greater than the TBN of the oil sample;
based on the TAN of the oil sample being greater than the TBN of the oil sample by a difference of about 3.02 or greater, evaluating two or more cationic surfactants for a treatment in at least a portion of the subterranean formation without evaluating any anionic surfactants for the treatment in the portion of the subterranean formation; and
introducing a treatment fluid into the subterranean formation at or above a pressure sufficient to create or enhance at least one fracture in the subterranean formation, the treatment fluid comprising at least one of the two or more cationic surfactants.

2. The method of claim 1 further comprising allowing molecules of the cationic surfactant introduced into the subterranean formation to form ion pairs with one or more anionic compounds in oil adsorbed onto a rock surface in a portion of the subterranean formation.

3. The method of claim 1 wherein at least one of the TAN and the TBN are measured at a laboratory at a site where a well bore penetrating at least a portion of the subterranean formation is located.

4. The method of claim 1 wherein the treatment fluid is introduced into the subterranean formation using one or more pumps.

5. The method of claim 1 wherein the subterranean formation comprises rock selected from the group consisting of: sandstone, limestone, shale, clay, and any combination thereof.

6. A method comprising:
providing a sample of oil from at least a portion of a subterranean formation;

determining the total acid number (TAN) and the total base number (TBN) of the oil sample by measuring the TAN and the TBN at a site where a well bore penetrating at least a portion of the subterranean formation is located, wherein the TBN of the oil sample is greater than the TAN of the oil sample;

based on the TBN of the oil sample being greater than the TAN of the oil sample by a difference of about 0.45 or greater, evaluating two or more anionic surfactants for a treatment in at least a portion of the subterranean formation without evaluating any cationic surfactants for the treatment in the portion of the subterranean formation; and introducing a treatment fluid into the subterranean formation at or above a pressure sufficient to create or enhance at least one fracture in the subterranean formation, the treatment fluid comprising at least one of the two or more anionic surfactants.

7. The method of claim 6 further comprising allowing molecules of the anionic surfactant introduced into the subterranean formation to form ion pairs with one or more cationic compounds in oil adsorbed onto a rock surface in a portion of the subterranean formation.

8. The method of claim 6 wherein at least one of the TAN and the TBN are determined by measuring at least one of the TAN and the TBN at a laboratory at a site where a well bore penetrating at least a portion of the subterranean formation is located.

* * * * *